US012788445B2

(12) United States Patent
Biedermann et al.

(10) Patent No.: US 12,788,445 B2
(45) **Date of Patent: *Nov. 10, 2026**

(54) ANCHORING MEMBER FOR A POLYAXIAL BONE ANCHORING DEVICE AND POLYAXIAL BONE ANCHORING DEVICE WITH SUCH AN ANCHORING MEMBER

(71) Applicant: BIEDERMANN TECHNOLOGIES GMBH & CO. KG, Donaueschingen (DE)

(72) Inventors: Timo Biedermann, Trossingen (DE); Achim Schunemann, VS-Mühlhausen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 19/041,422

(22) Filed: Jan. 30, 2025

(65) Prior Publication Data

US 2025/0241687 A1 Jul. 31, 2025

Related U.S. Application Data

(63) Continuation of application No. 17/665,837, filed on Feb. 7, 2022, now Pat. No. 12,232,776, which is a (Continued)

(30) Foreign Application Priority Data

Nov. 20, 2018 (EP) .................................... 18207354

(51) Int. Cl.

*A61B 17/70* (2006.01)
*A61B 17/86* (2006.01)
*A61B 17/00* (2006.01)

(52) U.S. Cl.

CPC ...... *A61B 17/7037* (2013.01); *A61B 17/7032* (2013.01); *A61B 17/8685* (2013.01); *A61B 2017/00867* (2013.01); *A61B 17/7059* (2013.01)

(58) Field of Classification Search

CPC ............ A61B 17/7037; A61B 17/7032; A61B 17/7059; A61B 17/8685; A61B 2017/00867

(Continued)

(56) References Cited

U.S. PATENT DOCUMENTS 5,443,467 A 8/1995 Biedermann et al.
11,284,922 B2 * 3/2022 Biedermann ...... A61B 17/7037

(Continued)

FOREIGN PATENT DOCUMENTS

CN 103860247 A 6/2014

OTHER PUBLICATIONS

Extended European Search Report for Application No. 18207354.4, mailed May 27, 2019, 7 pages.

*Primary Examiner* — Eduardo C Robert
*Assistant Examiner* — David C Comstock
(74) *Attorney, Agent, or Firm* — Womble Bond Dickinson (US) LLP

(57) ABSTRACT

An anchoring member for a polyaxial bone anchoring device includes a bone anchoring section having a first end, a second end, and a bone engagement structure, a head having an outer surface portion that defines a segment of a sphere, wherein a central axis extends through the head and the first and second ends of the bone anchoring section, and a neck extending between the first end of the bone anchoring section and the head. The neck has a first portion and a second portion between the first portion and the bone anchoring section. In at least a first cross-sectional plane (Continued)

including the central axis, the first portion of the neck is concave with a first curvature, and the second portion of the neck is concave with a second curvature that is less curved than the first curvature.

20 Claims, 6 Drawing Sheets

Related U.S. Application Data continuation of application No. 16/686,714, filed on Nov. 18, 2019, now Pat. No. 11,284,922.

(60) Provisional application No. 62/769,854, filed on Nov. 20, 2018.

(58) Field of Classification Search
USPC ................ 606/266, 270, 287, 305, 308, 279
See application file for complete search history.

(56) References Cited

U.S. PATENT DOCUMENTS

| | | | | |
|---|---|---|---|---|
| 12,232,776 | B2 * | 2/2025 | Biedermann | A61B 17/7037 |
| 2006/0276789 | A1 | 12/2006 | Jackson | |
| 2008/0319490 | A1 | 12/2008 | Jackson | |
| 2009/0163961 | A1 | 6/2009 | Kirschman | |
| 2010/0198272 | A1 | 8/2010 | Keyer et al. | |
| 2010/0262196 | A1 | 10/2010 | Barrus et al. | |
| 2011/0040338 | A1 | 2/2011 | Jackson | |
| 2011/0282399 | A1 | 11/2011 | Jackson | |
| 2012/0059425 | A1 | 3/2012 | Biedermann | |
| 2014/0142632 | A1 | 5/2014 | Keyer et al. | |
| 2014/0172018 | A1 | 6/2014 | Gephart et al. | |
| 2014/0188174 | A1 | 7/2014 | Biedermann et al. | |
| 2014/0214097 | A1 | 7/2014 | Jackson et al. | |
| 2015/0282844 | A1 | 10/2015 | Vedula et al. | |
| 2017/0245894 | A1 | 8/2017 | Ramsay et al. | |
| 2018/0092664 | A1 | 4/2018 | Schluzas | |

* cited by examiner

ANCHORING MEMBER FOR A POLYAXIAL BONE ANCHORING DEVICE AND POLYAXIAL BONE ANCHORING DEVICE WITH SUCH AN ANCHORING MEMBER

CROSS-REFERENCE TO RELATED APPLICATION(S)

This application is a continuation of U.S. patent application Ser. No. 17/665,837, filed Feb. 7, 2022, which is a continuation of U.S. patent application Ser. No. 16/686,714, filed Nov. 18, 2019, now U.S. Pat. No. 11,284,922, which claims priority to and the benefit of U.S. Provisional Patent Application No. 62/769,854, filed Nov. 20, 2018, the contents of which are hereby incorporated by reference in their entirety, and claims priority from European Patent Application EP 18 207 354.4, filed Nov. 20, 2018, the contents of which are hereby incorporated by reference in their entirety.

BACKGROUND

Field

The application relates to an anchoring member for a polyaxial bone anchoring device and to a polyaxial bone anchoring device including the anchoring member. In particular, the application is related to devices for the treatment of spinal disorders or for use in trauma surgery.

Description of Related Art

Polyaxial bone anchoring devices for use in the treatment of spinal disorders are well known in the art. For example, U.S. Pat. No. 5,443,467 describes a polyaxial bone anchoring device with an anchoring element comprising a shaft for anchoring in bone and a spherical segment-shaped head, wherein the anchoring element is pivotably held in a receiving part that is configured to couple the anchoring element to a spinal rod.

US 2017/0245894 A1 describes a polyaxial bone anchoring device comprising an anchor body and a fastener that includes a head, a threaded shaft that extends out with respect to the head in a distal direction, and a neck between the head and the threaded shaft. The head includes an outer surface, at least a portion of which is convex and defines a portion of a sphere that defines a first diameter. The neck defines a second diameter, and the fastener defines a ratio of the first diameter to the second diameter in a range between about 2 to 1 and about 3 to 1.

SUMMARY

A portion of an anchoring element or anchoring member located between a head and a shaft may be a potential area where the anchoring member may fail under load.

It is an object of the invention to provide an anchoring member and a polyaxial bone anchoring device including the anchoring member that is improved with respect to a possible failure under load.

According to an aspect of the disclosure, an anchoring member for a polyaxial bone anchoring device includes a bone anchoring section having a first end, a second end, and a bone engagement structure on at least a portion thereof, a head having an outer surface portion that defines a portion of a sphere, a central axis extending through respective centers of the head and the first and second ends of the bone anchoring section, and a neck between the first end of the bone anchoring section and the head, the neck including a first portion that is closer to the head than to the bone anchoring section, wherein in at least one plane including the central axis, the first portion of the neck is concave with a first curvature, the neck further including a second portion between the first portion and the bone anchoring section, wherein in the at least one plane, the second portion is concave with a second curvature that is smaller or less curved than the first curvature. On at least one side of or in at least one radial direction relative to the central axis, the first portion joins the second portion in an axial direction.

By means of this design, a transition between the bone anchoring section or a cylindrical portion of the neck and the head is shifted toward a center of the head in the axial direction. Thereby the distribution of loads acting onto the head and/or the neck is improved. As a result, the strength, in particular the fatigue strength, of the anchoring member against breaking, in particular in the region of the neck, is increased.

According to another aspect of the disclosure, a polyaxial bone anchoring device includes the anchoring member and a receiving part including a seat configured to receive the head of the anchoring member, such that the bone anchoring section can assume a plurality of angular positions relative to the receiving part.

A maximum pivot angle that the anchoring member can form relative to the receiving part may also be increased compared to an anchoring member that has a substantially cylindrical neck.

BRIEF DESCRIPTION OF THE DRAWINGS

Further features and advantages will become apparent from the description of embodiments by means of the accompanying drawings. In the drawings.

DETAILED DESCRIPTION

Figure 1:
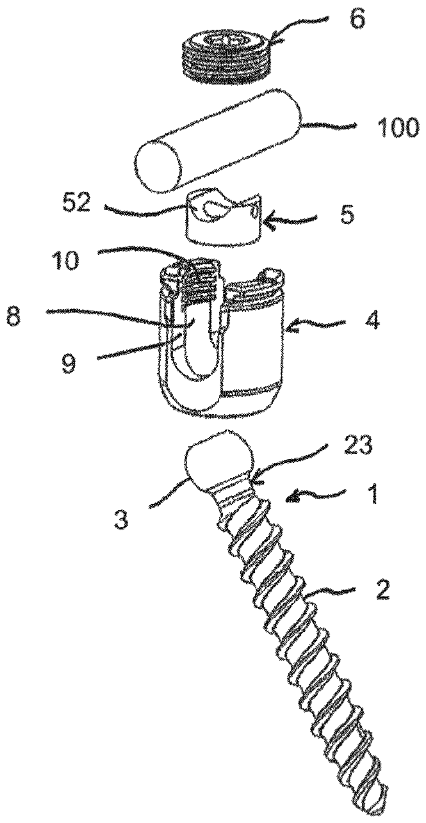
FIG. 1 shows a perspective exploded view of a polyaxial bone anchoring device according to a first embodiment of the invention.
Figure 2:
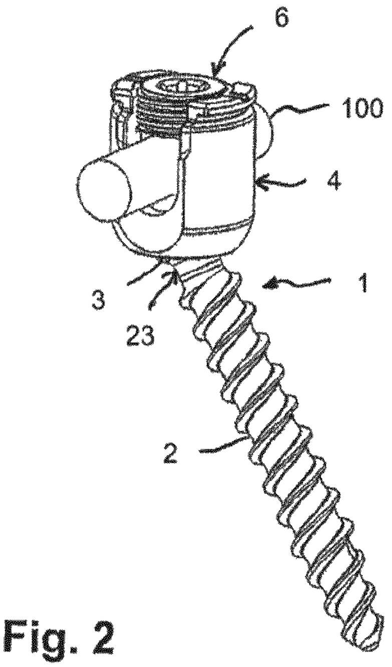
FIG. 2 shows a perspective view of the polyaxial bone anchoring device of FIG. 1 in an assembled state.

Referring to FIGS. 1 and 2, a polyaxial bone anchoring device according to a first embodiment includes an anchoring member 1 including a shank 2 for anchoring in a bone or a vertebra, and a head 3. Further, a receiving part 4 for pivotably receiving the head 3 of the anchoring member 1 is provided that is configured to couple the anchoring member 1 to a stabilization rod 100. Moreover, a pressure member 5 may be provided to exert pressure onto the head 3 in the receiving part 4, to lock the head 3 in a specific angular position with respect to the receiving part 4. Furthermore, a locking member 6, for example in the form of a set screw, may be part of the bone anchoring device for securing and fixing rod 100 in the receiving part 4.

Figure 5:
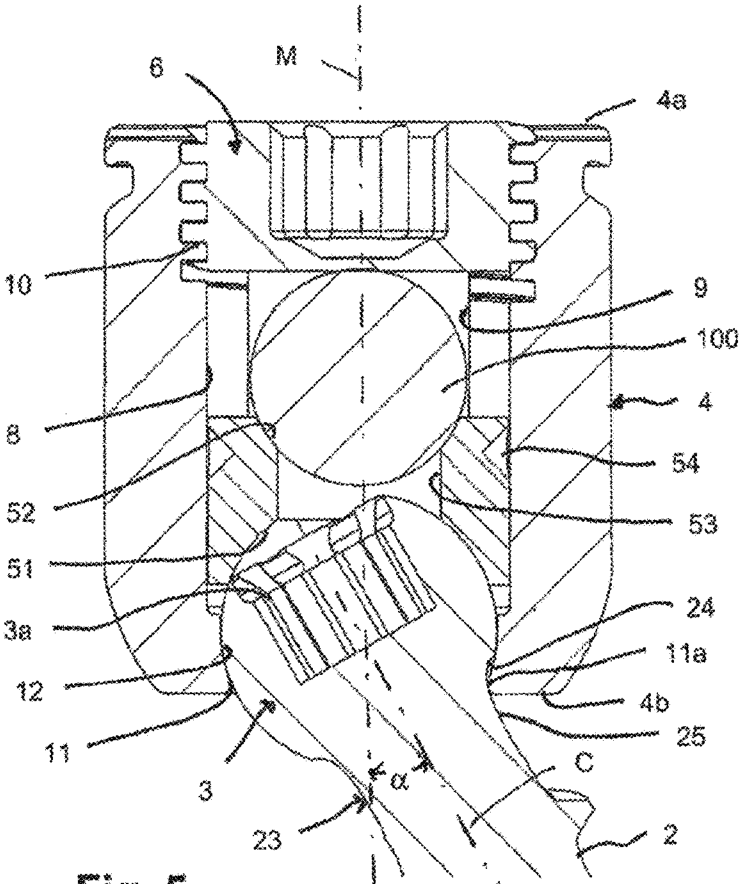
FIG. 5 shows a cross-sectional view of the bone anchoring device according to FIGS. 1 and 2, with the cross-section taken in a plane extending through a center of a head of the anchoring member and perpendicular to a longitudinal axis of a rod received by the bone anchoring device.

As can be seen additionally in FIG. 5, the receiving part 4 has a first end or top end **4*a* and an opposite second end or bottom end 4*b*, an axis of symmetry M and a coaxial bore 8 extending from the first end 4*a* in the direction of the second end 4*b*. Adjacent to the first end 4*a*, a substantially U-shaped recess 9 is provided that serves as a channel for receiving the rod 100. By means of the recess 9, two free legs are formed which are provided with an engagement structure, such as an internal thread 10, for cooperating with the locking member 6**.

Adjacent to or close to the second end, the passage provided by the coaxial bore 8 narrows towards the second end **4*b* and forms an opening 11, whose inner diameter is of a size such that the anchoring member 1 can be guided through with the shank 2 until the head 3 is seated in a seat 12 adjacent to the opening 11. The seat 12 for the head 3 may be designed as a spherical segment-shaped portion that matches an outer surface portion of the head 3**.

Figure 3:
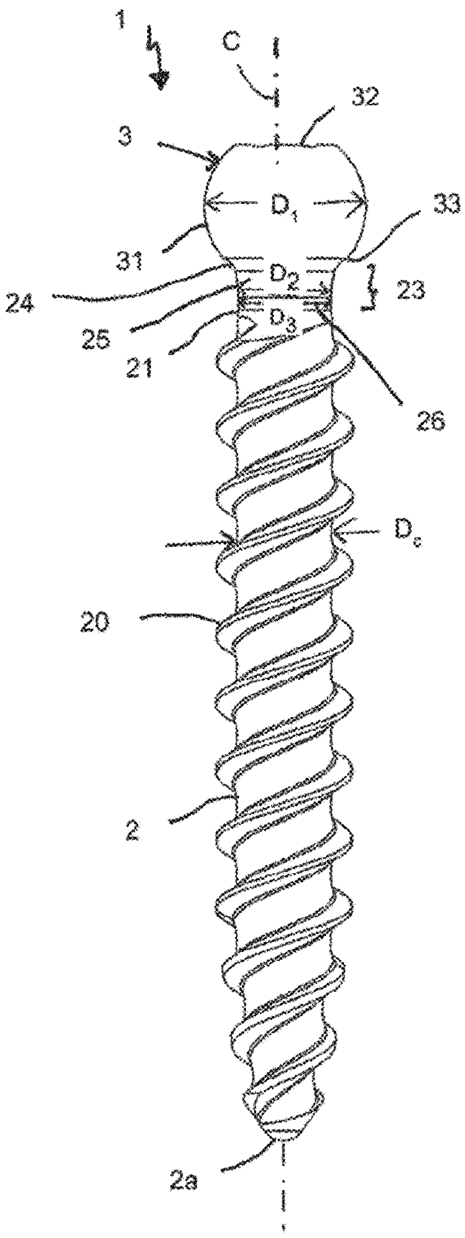
FIG. 3 shows a side view of an anchoring member of the polyaxial bone anchoring device according to the first embodiment.
Figure 4:
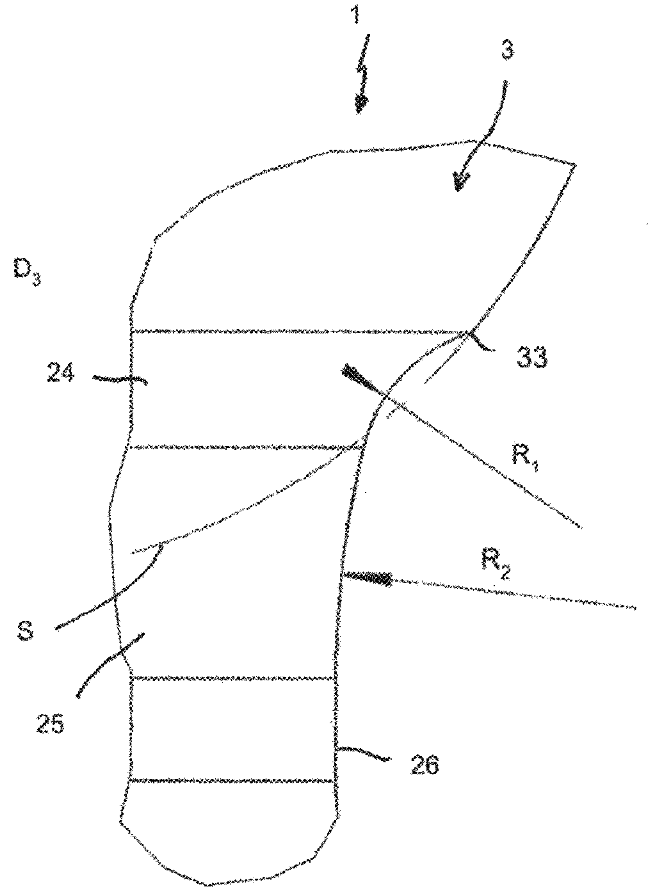
FIG. 4 shows an enlarged view of a portion of the anchoring member of FIG. 3.

Referring now further to FIGS. 3 and 4, the anchoring member 1 has a central axis C extending through a center of the head 3 and being coaxial to a longitudinal axis of the shank 2. Preferably, the anchoring member 1 is a monolithic piece. The shank 2 has a first end 21 facing the head 3 and an opposite second end 22 that may be shaped as a tip. On at least a portion of the outer surface of the shank 2, a bone engagement structure 20, for example a bone thread, may be provided. Hence, the shank 2 forms a bone anchoring section of the anchoring member 1. The head 3 has a spherically-shaped outer surface portion 31 that defines a sphere S (see FIG. 4) with a diameter $D_1$. In greater detail, in the embodiment, the head 3 has an axial length, such that the diameter $D_1$ of the sphere S forms the largest width of the head 3. A section of the sphere S in a plane P that includes the central axis C forms part of a circle (see for example FIG. 6). At the side opposite to the second end 22 of the shank, the head 3 has a free end surface 32 that may include a recess **3*a* for engagement with a driver to drive the anchoring member 1 into bone. The free end surface 32** may be flat.

Between the head 3 and the first end 21 of the shank 2, a neck 23 is formed. The neck 23 includes a first portion 24 that is closer to the head 3 and a second portion 25 that is closer to the bone anchoring section. The first portion 24 has an outer surface that is concave with a first curvature. In the plane P, the surface of the first portion 24 of the neck 23 defines a circular segment with a first radius of curvature $R_1$. Preferably, the neck 23 and the outer surface portion 31 of the head 3 are rotationally symmetrical around the central axis C. Hence, the first radius of curvature $R_1$ of the first portion 24 is the same in every radial direction, and therefore in every plane that includes the central axis C. At the position where the first portion 24 of the neck 23 meets the head 3, an edge 33 is formed. By the concave shape of the first portion 24, the width of the anchoring member decreases from the head 3 towards the shank 2.

The second portion 25 of the neck 23 is also concave, with a second curvature that is smaller than the first curvature. In other words, the surface of the second portion 25 is less strongly curved than that of the first portion 24. In the embodiment, the surface of the second portion 25 also defines a circular segment in the plane P, with a second radius of curvature $R_2$ that is greater than $R_1$, as depicted in FIG. 4. Due to the rotational symmetry, the second radius of curvature $R_2$ of the second portion 25 of the neck 23 is the same in every radial direction, and therefore in every plane that includes the central axis C. As can be seen in the figures, the first portion 24 continuously merges into the second portion 25.

A diameter $D_2$ of the neck 23 in a plane perpendicular to the central axis C is, at any axial position of the first portion 24 or the second portion 25, smaller than the first diameter $D_1$. More specifically, in the second portion 25, the diameter $D_2$ is such that a ratio $D_1$:$D_2$ is about 7:4. Preferably, the ratio $D_1$:$D_2$ may be between about 1 and about 2. An axial length of the second portion 25 is greater than an axial length of the first portion 24. More specifically, the axial length of the second portion 25 may be two times as long or more than the axial length of the first portion 24.

Between the second portion 25 and the shank 2, a third, cylindrical portion 26 may be provided. The second portion 25 continuously merges into the cylindrical portion 26. An axial length of the third, cylindrical portion 26 may be smaller than an axial length of the second portion 25. The outer diameter $D_3$ of the third cylindrical portion 26 may be the same as or slightly greater than a core diameter $D_c$ of the shank 2. At the transition between the second portion 25 and the cylindrical portion 26, $D_3$ may be the same as $D_2$.

The pressure member 5 will now be explained, with reference to FIGS. 1 and 5. The pressure member 5 may be formed as a monolithic piece, may be of substantially cylindrical construction, and has an outer diameter that allows it to move in the axial direction within the bore 8 of the receiving part 4. Moreover, the pressure member 5 has a substantially spherical recess 51 at its side that faces the head 3 when the pressure member 5 and the head 3 are assembled within the receiving part 4. The substantially spherical recess 51 is adapted to the size of the head 3. At the opposite side facing away from the head 3, a substantially cylindrically-shaped recess 52 is formed that is configured to receive the rod 100 therein. In this embodiment, the surface of the rod extends above the sidewalls of the recess 52 when the rod 100 is inserted into the recess 52. A coaxial bore 53 formed in the pressure member 5 permits access with a tool such as a driver to the recess **3*a* in the head 3 when the head 3 of the anchoring member 1 is assembled in the receiving part 4**.

The locking member 6 may be formed as a set screw that can be screwed between the legs of the receiving part 4. The locking member 6 is configured to contact the rod 100 when the rod 100 is inserted into the receiving part 4.

The anchoring member 1, the receiving part 4, the pressure member 5, and the locking member 6, as well as the rod

100, may each be made of one or more bio-compatible materials, for example of titanium or stainless steel, of a bio-compatible alloy, such as NiTi-alloys, for example Nitinol, of magnesium or magnesium alloys, or from a bio-compatible plastic material, such as, for example polyether ether ketone (PEEK) or poly-L-lactide acid (PLLA). In addition, the parts can be made of the same as or of different materials from another.

Figure 6:
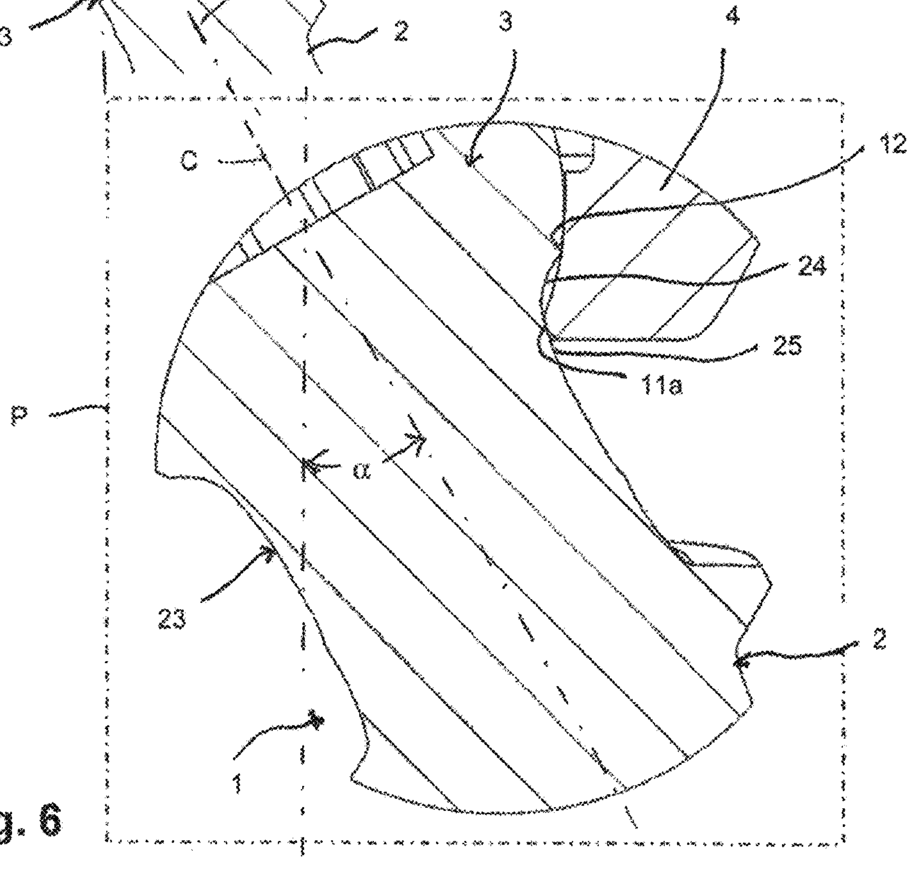
FIG. 6 shows an enlarged view of a portion of FIG. 5.
Figure 7:
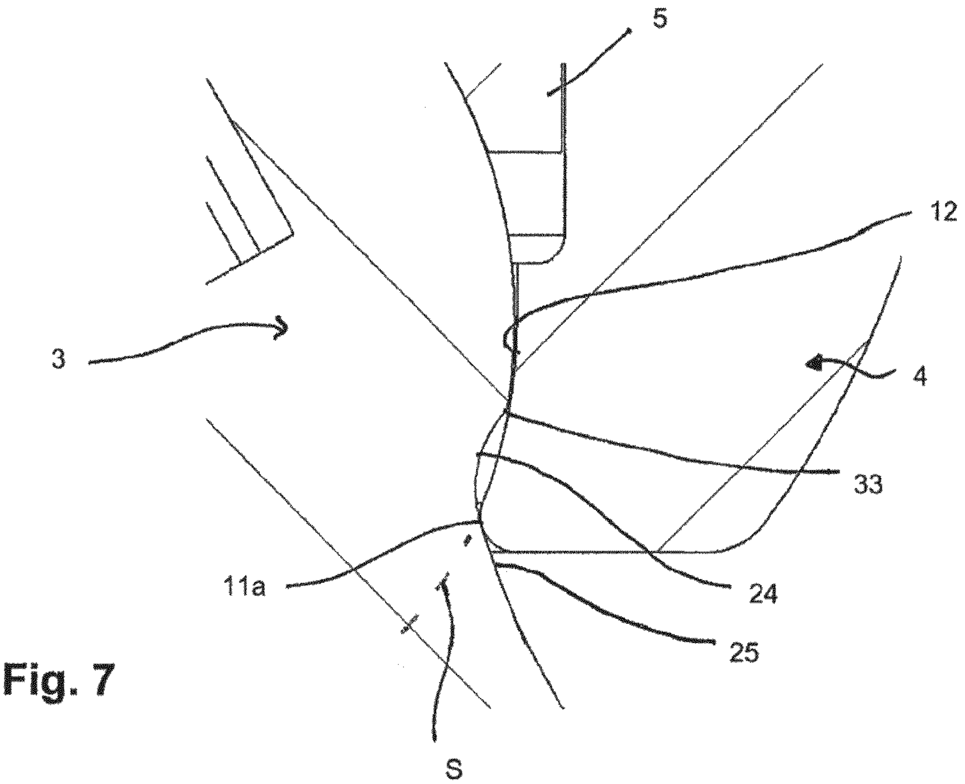
FIG. 7 shows a further enlarged view of the bone anchoring device of FIG. 5.

Turning now to FIGS. 5 to 7, the polyaxial bone anchoring device may be preassembled with the anchoring member 1 being inserted from the first end 4*a* into the receiving part 4 until its head 3 rests in the seat 12. The pressure member 5 may be rotationally fixed within the receiving part 4, for example, by crimping using crimp bores 54 at the outer surface of the pressure member 5.

In use, at least two anchoring members 1 with receiving parts 4 are inserted into the bone or in adjacent vertebrae and connected through the rod 100. For inserting the rod 100 into a receiving part 4, the receiving part 4 may be pivoted relative to the anchoring member 1 to facilitate insertion of the rod 100. As shown in FIGS. 5 and 6, a maximum pivot angle α is defined by the abutment of the neck 23 against an edge 11*a* of the opening 11 of the receiving part 4. The sizes of the head 3 and the neck 23 relative to the seat 12 in the receiving part 4 are such that the edge 11*a* abuts against the second portion 25 of the neck that has the smaller or less curved curvature. In the position of the maximum pivot angle α, the first portion 24 of the neck 23 is preferably located within the seat 12 of the receiving part 4 at the side to which the anchoring member 1 pivots.

Figure 8:
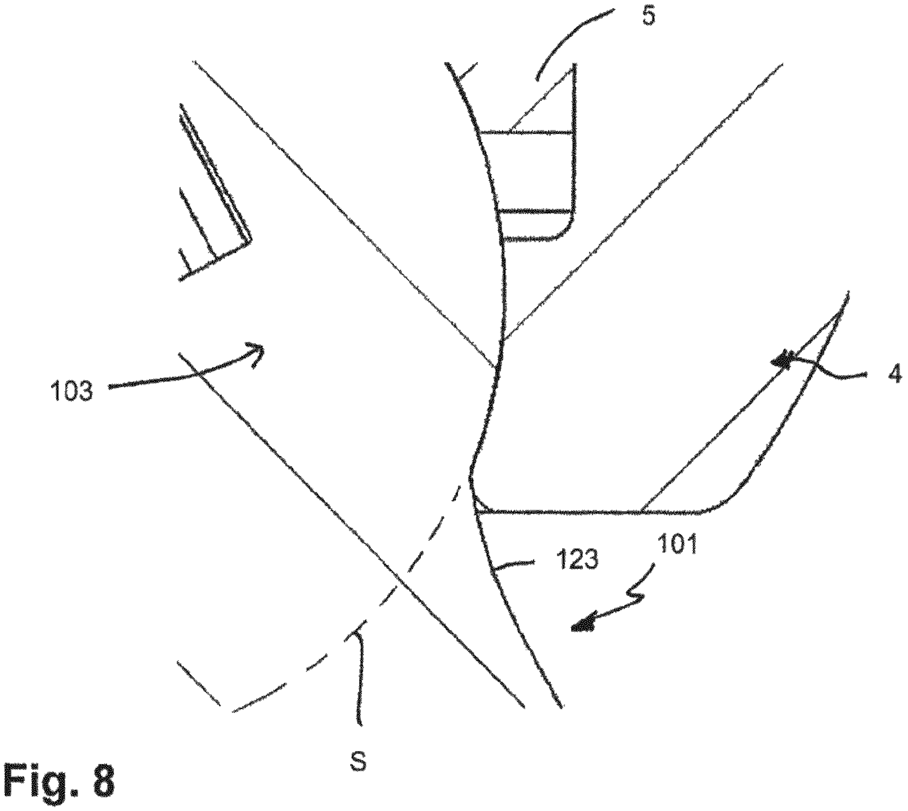
FIG. 8 shows, in comparison to FIG. 7, an enlarged view of a portion of a bone anchoring device including an example of an anchoring member that has a substantially cylindrical neck.

Referring to FIG. 8, a comparative example of an anchoring member 101 is shown in which the neck 123 is devoid of any portions that extend into the sphere S defined by the spherical segment-shaped head 103. Comparing the anchoring member of the embodiment according to FIG. 7 with the example of the anchoring member of FIG. 8, the maximum pivot angle α is increased when the neck 23 extends into the sphere S, as shown in FIG. 7. Moreover, the strength of the anchoring member 1 of the embodiment shown in FIG. 7 against loads is increased. Ultimately, forces can be distributed in an improved manner between the head 3 and the neck 23.

Figure 9:
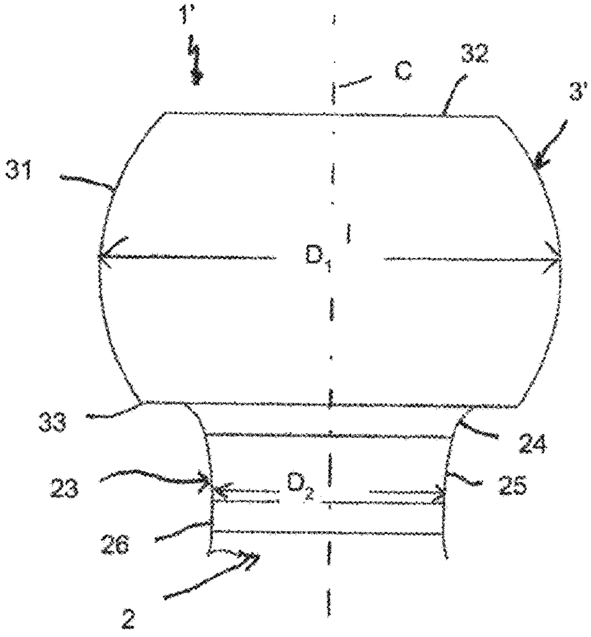
FIG. 9 shows a side view of a portion of an anchoring member according to a second embodiment of the invention.
Figure 10:
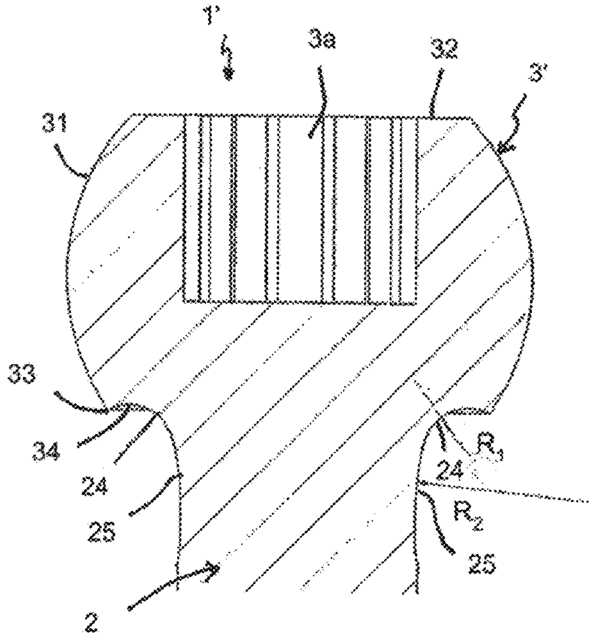
FIG. 10 shows a cross-sectional view of the anchoring member of FIG. 9, the cross-section taken in a plane including a central axis of the anchoring member.
Figure 11:
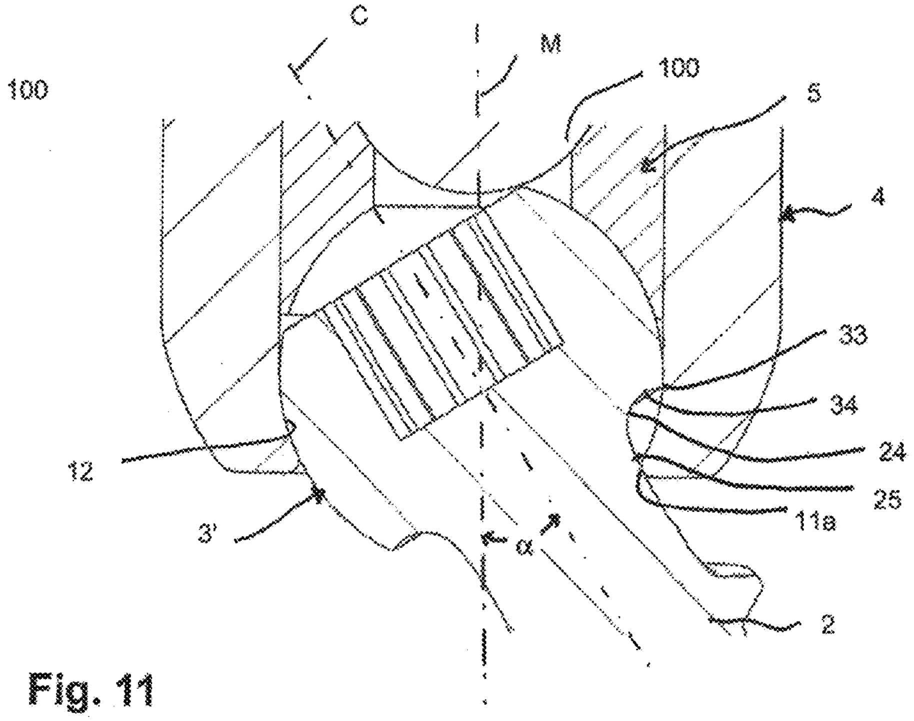
FIG. 11 shows a cross-sectional view of a portion of a bone anchoring device according to the second embodiment of the anchoring member shown in FIGS. 9 and 10, with the cross-section taken in a plane extending through the center of the head of the anchoring member and perpendicular to the longitudinal axis of a rod received by the bone anchoring device.

Referring to FIGS. 9 to 11, a second embodiment of the anchoring member will be described. The anchoring member 1' differs from the anchoring member 1 of the first embodiment by the shape and size of the head. All other portions are identical or similar, and the descriptions thereof will not be repeated. Like portions are provided with the same reference numerals as in the first embodiment. The head 3' of the anchoring member 1' has a diameter $D_1'$ that, when compared relative to the diameter $D_2$ of the neck 23, is relatively larger than the diameter $D_1$ of the anchoring member 1 of the first embodiment. More specifically, the ratio of $D_1':D_2$ may be between about 1 and about 3. At the side opposite to the free end surface 32, the head includes an undercut portion 34 that extends between the edge 33 and the first portion 24 of the neck 23. The undercut portion 34 is recessed from a virtual plane that extends perpendicular to the central axis C and through the outermost point of the edge 33, in a direction towards the free end surface 32. Preferably, the undercut portion 34 is curved in the same manner as the first portion 24 of the neck 23. In greater detail, in the embodiment, the surface of the undercut portion 34 defines part of the circular segment in the plane P that continues from the second portion 24 to the edge 33. Hence, the radius of curvature $R_1$ of the undercut portion 34 and that of the first portion 24 of the neck 23 may be the same. However, the undercut portion 34 may also have another shape, for example a non-circular curvature.

By means of this design, the strength of the anchoring member can be further increased. As illustrated in FIG. 11, due to the enlarged diameter of the head 3', the maximum pivot angle α can be further increased.

Figure 12:
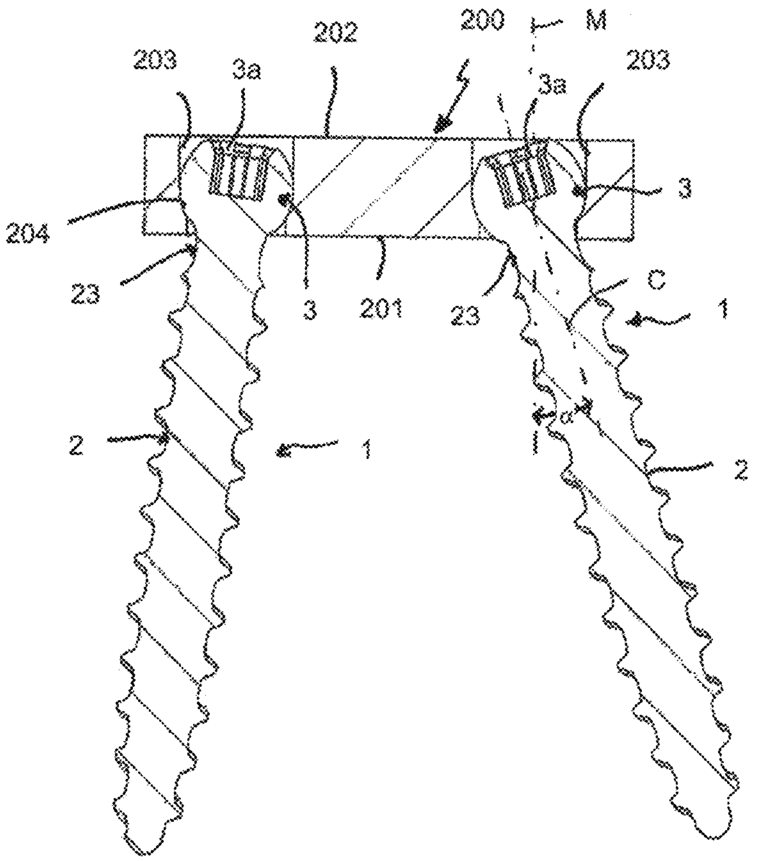
FIG. 12 shows a cross-sectional view of a still further embodiment of a polyaxial bone anchoring device, in the form of a bone plate.

Referring to FIG. 12, a second embodiment of a polyaxial bone anchoring device is shown that includes a bone plate 200 as a receiving part for the anchoring member 1. The bone plate 200 has a first or bone-contacting surface 201 and an opposite second surface 202. At least one, preferably more than one through-hole 203 extends from the second surface 202 through the plate to the first surface 201. In the wall that defines the through-hole 203, a seat 204 is formed for the head 3 of the anchoring member 1. The seat 204 has a shape corresponding to the outer spherical-surface portion of the head 3 so that, as long the bone plate and the anchoring member 1 are not implanted into the body, the anchoring member 1 can pivot within the seat 204 with a maximum pivot angle α to at least one side. The anchoring member is, for example, the anchoring member 1 of the first embodiment or may be the anchoring member 1' of the second embodiment. In use, the anchoring member can be inserted into the bone at a specific angle that is delimited by the maximum pivot angle of the polyaxial bone anchoring device. The strength of the anchoring member under load is improved. If necessary, a locking cap (not shown) may further be provided in the hole 203 to prevent backing-out of the anchoring member.

The polyaxial bone anchoring device is not limited to the embodiments shown. The anchoring member can be used with any receiving part that provides a seat for the head. Such receiving parts can be of the top-loading type, where the anchoring member is inserted from the top of the receiving part, or of the bottom-loading type, where the anchoring member is inserted with the head through a lower opening. Also, any bone plate or other surgical implant that is combined with an anchoring member of the above described embodiments can form a polyaxial bone anchoring device according to embodiments of the invention. The seat may have another shape, and/or may be provided within an insert member that is within the receiving part. Many different polyaxial bone anchoring devices may be conceivable.

Modifications of the anchoring member are also conceivable. For example, the bone anchoring section may have any bone anchoring structure or shape that is suitable for anchoring in bone or in a vertebra. The head may also be non-rotationally symmetrical. For example, the head may have two opposite flat surface portions, so that the spherical surface portion allows the anchoring member to pivot in the receiving part only in a single plane. The symmetry of the neck may correspond to the symmetry of the head.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An anchoring member for a polyaxial bone anchoring device, the anchoring member comprising:

a bone anchoring section having a first end, a second end, and a bone engagement surface on at least a portion thereof;

a head having a free end opposite the bone anchoring section and an outer surface extending from the free end towards the bone anchoring section with a portion that defines a segment of a sphere, wherein a central axis extends through respective centers of the head and the first and second ends of the bone anchoring section; and a neck extending between the first end of the bone anchoring section and the head;

wherein an undercut that is formed at a side of the head that faces the neck has a portion that extends back towards the free end of the head.

2. The anchoring member of claim 1, wherein the neck extends substantially rotationally symmetrically around the central axis.

3. The anchoring member of claim 1, wherein an edge is formed at a lowermost end of the segment of the sphere formed by the head.

4. The anchoring member of claim 3, wherein the edge is rounded.

5. The anchoring member of claim 1, wherein the segment of the sphere defined by the outer surface portion of the head has a diameter, and wherein the neck has a width in a plane perpendicular to the central axis, such that a ratio between the diameter and the width is greater than 1 and less than 2.

6. The anchoring member of claim 5, wherein the ratio between the diameter and the width is about 7:4.

7. A polyaxial bone anchoring device comprising:

the anchoring member of claim 1; and a receiving part defining an accommodation space for accommodating the head of the anchoring member such that the bone anchoring section of the anchoring member can assume a plurality of angular positions relative to the receiving part.

8. The anchoring member of claim 1, wherein the neck comprises a first portion having at least a region that is closer to the head than to the bone anchoring section, and a second portion extending between the first portion and the bone anchoring section, and wherein in at least a first cross-sectional plane including the central axis, the first portion is concave with a first curvature, while the second portion is concave with a second curvature that is less curved than the first curvature.

9. The anchoring member of claim 8, wherein at least part of the second portion extends outside of a circle defined by the segment of the sphere of the head.

10. An anchoring member for a polyaxial bone anchoring device, the anchoring member comprising:

a bone anchoring section having a first end, a second end, and a bone engagement surface on at least a portion thereof;

a head having an outer surface portion that defines a segment of a sphere, wherein a central axis extends through respective centers of the head and the first and second ends of the bone anchoring section; and a neck extending between the first end of the bone anchoring section and the head, the neck comprising:

a first portion having at least a region that is closer to the head than to the bone anchoring section, wherein in at least a first cross-sectional plane including the central axis, the first portion is concave with a first curvature; and a second portion extending between the first portion and the bone anchoring section, wherein in at least the first cross-sectional plane, the second portion is concave with a second curvature that is less curved than the first curvature, with at least part of the second portion extending outside of a circle defined by the segment of the sphere.

11. The anchoring member of claim 10, wherein in at least the first cross-sectional plane, another part of the second portion of the neck is positioned in the circle.

12. The anchoring member of claim 10, wherein in at least the first cross-sectional plane, the first portion of the neck is positioned completely within the circle.

13. The anchoring member of claim 10, wherein the neck extends substantially rotationally symmetrically around the central axis.

14. The anchoring member of claim 10, wherein the first curvature has a first radius of curvature, and wherein the second curvature has a second radius of curvature that is greater than the first radius of curvature.

15. The anchoring member of claim 10, wherein a cylindrical portion extends between the second portion of the neck and the bone anchoring section.

16. A polyaxial bone anchoring device comprising:

a monolithic anchoring member comprising:

a bone anchoring section having a first end, a second end below the first end, and a bone engagement surface on at least a portion thereof;

a head having a free end opposite the bone anchoring section and an outer surface extending from the free end towards the bone anchoring section with a portion that defines a segment of a sphere, wherein a central axis extends through respective centers of the head and the first and second ends of the bone anchoring section; and a neck extending between the first end of the bone anchoring section and the head, wherein a first portion of the neck is concave with at least a portion that extends into a sphere defined by the outer surface of the head, and wherein at least the first portion of the neck extends substantially rotationally symmetrically around the central axis; and a receiving part that defines an accommodation space for accommodating the head of the anchoring member such that the bone anchoring section of the anchoring member can assume a plurality of angular positions relative to the receiving part, and a rod receiving recess for receiving an elongate rod, wherein the rod receiving recess forms two legs each having an engagement surface configured to engage a locking member between the two legs for locking the rod in the rod receiving recess;

wherein when the head is held in the accommodation space and the anchoring member is pivoted to a maximum pivot angle relative to the receiving part, the entire free end of the head of the anchoring member remains positioned axially higher than a lowermost end of the receiving part.

17. The polyaxial bone anchoring device of claim 16, wherein the neck further comprises a second portion that extends between the first portion and the bone anchoring section, and wherein in at least a first cross-sectional plane including the central axis, the first portion is concave with a first curvature, while the second portion is concave with a second curvature that is less curved than the first curvature.

18. The polyaxial bone anchoring device of claim 17, wherein at least part of the second portion extends outside of a circle defined by the segment of the sphere of the head.

19. The polyaxial bone anchoring device of claim 16, wherein an edge is formed at a lowermost end of the segment of the sphere formed by the head.

20. The polyaxial bone anchoring device of claim 19, wherein the edge is rounded.

* * * * *